United States Patent [19]

Shaposka et al.

[11] Patent Number: 4,864,101
[45] Date of Patent: Sep. 5, 1989

[54] HYBRID WELDING WAFER

[75] Inventors: John B. Shaposka; Dudley W. Spencer, both of Wilmington, Del.

[73] Assignee: Denco, Inc., Wilmington, Del.

[21] Appl. No.: 1,955

[22] Filed: Jan. 9, 1987

[51] Int. Cl.[4] .......................... B26D 7/10; B29C 65/20
[52] U.S. Cl. ........................................ 219/243; 30/115;
30/140; 83/171; 156/499; 156/510; 219/233;
219/543
[58] Field of Search .................... 156/499, 158, 304.2,
156/304.6, 510, 289, 583.2; 219/243, 254, 543,
538, 552, 553, 233; 604/905; 83/171, 922;
30/115, 140

[56] References Cited

U.S. PATENT DOCUMENTS

| | | | |
|---|---|---|---|
| 2,859,321 | 11/1958 | Garaway | 219/543 |
| 4,369,779 | 1/1983 | Spencer | 604/905 |
| 4,412,123 | 10/1983 | Ammann et al. | 156/583.2 |
| 4,412,835 | 11/1983 | Spencer | 604/905 |
| 4,501,951 | 2/1985 | Benin et al. | 156/304.6 |
| 4,507,119 | 3/1985 | Spencer | 604/905 |
| 4,516,671 | 5/1985 | Spencer | 604/905 |
| 4,521,263 | 6/1985 | Benin et al. | 156/159 |
| 4,610,670 | 9/1986 | Spencer | 604/905 |
| 4,619,642 | 10/1986 | Spencer | 604/905 |
| 4,622,966 | 11/1986 | Beard | 30/140 |

Primary Examiner—Michael Wityshyn
Attorney, Agent, or Firm—Connolly & Hutz

[57] ABSTRACT

A thin wafer for cutting plastic tubes which are to be butt welded together includes a high temperature insulated plate-like core with a resistance circuit on the core for heating the wafer to a temperature sufficiently high to melt through the tubes. A glass layer may be on the outer surface of the water, particularly in the contact area with the tube. The wafer may be used in an arrangement wherein residue is removed from the water by having the residue adhere to unused portions or stubs of the tubes which then would be stripped from the wafer.

3 Claims, 3 Drawing Sheets

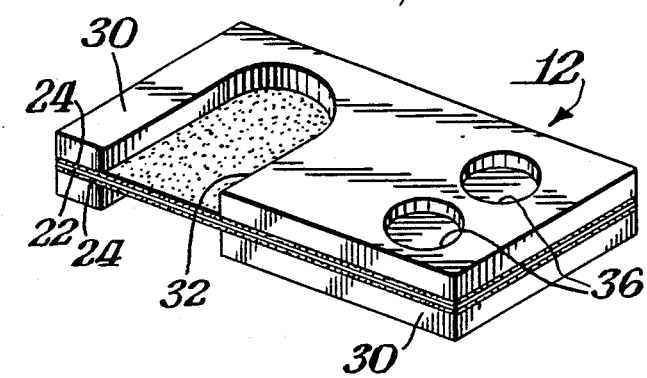
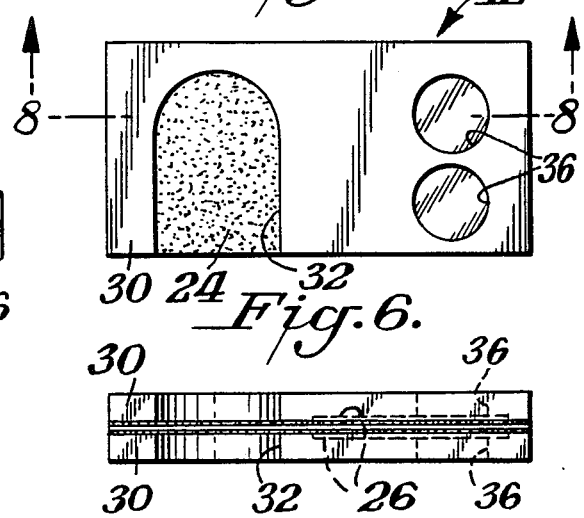
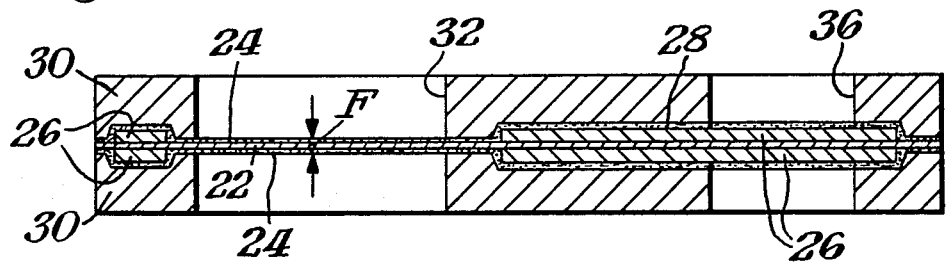
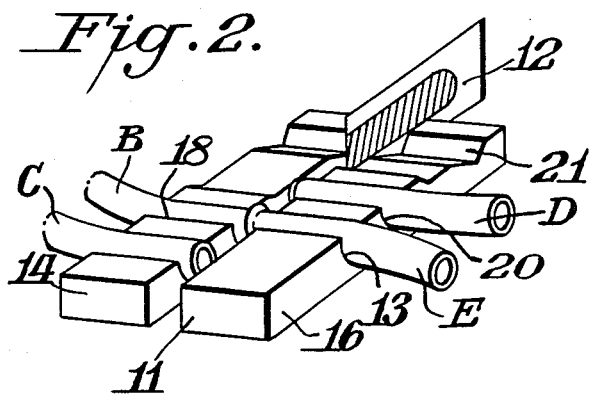
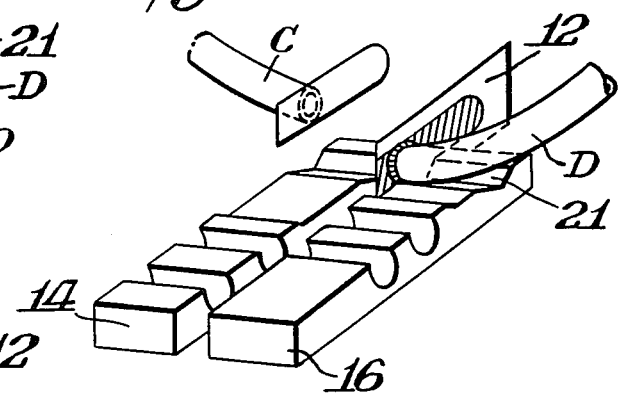
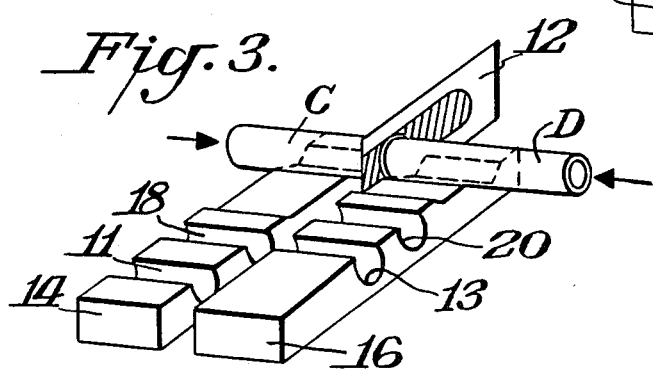

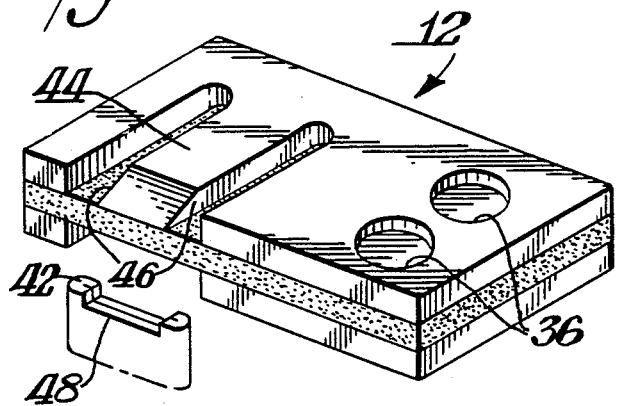
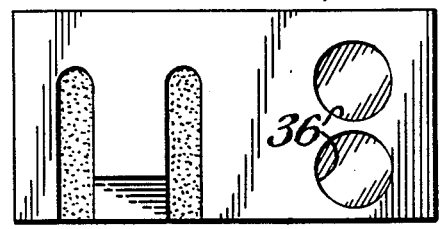
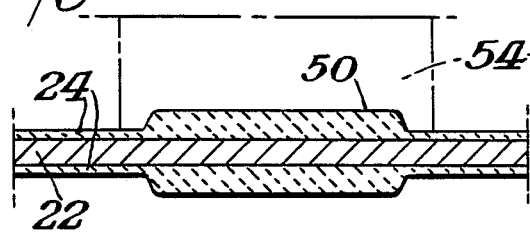
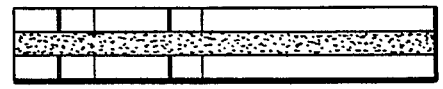
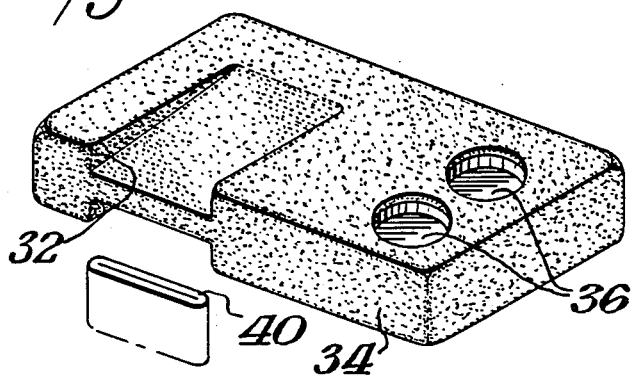
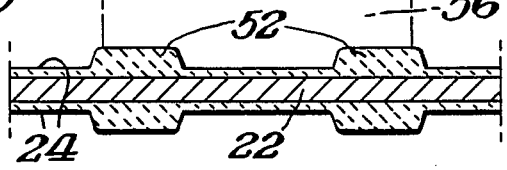
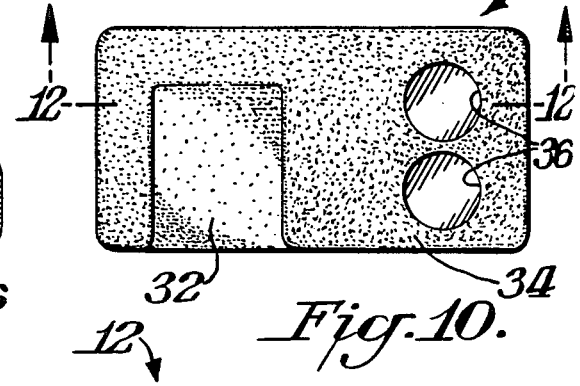
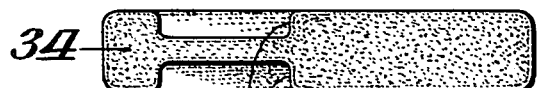
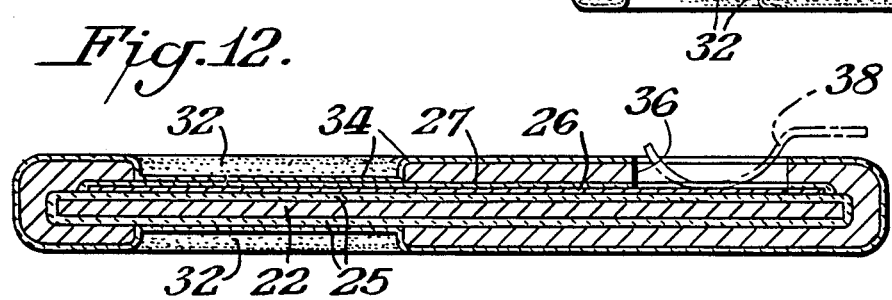

HYBRID WELDING WAFER

BACKGROUND OF THE INVENTION

The present invention is related to the field of cutting plastic tubes which are to be butt welded together. Such a field includes the attempt to provide a sterile connection between two tubes for medical or scientific purposes. For example, the invention would relate to the sterile docking in continuous ambulatory peritoneal dialysis. U.S. Pat. Nos. 4,369,779 and 4,610,670 are generally directed to such types of systems. A commercial practice of those patents is in a device marketed under the name SCD.

Thermoplastic tubing can be butt welded together by any number of means. In one such method the tubes are positioned side-by-side and severed by a hot knife (welding wafer). The severed tubes are then re-positioned while still in contact with the wafer, the wafer is then removed, and the tube ends are pressed together to make the weld. Since the wafer must reach temperatures well above the melting point of the tube material, the melting tube typically leaves a residue on the side of the wafer. This residue must either be removed or a new wafer used for the next weld. This residue problem results in the need for a number of costly parts in the welding device:

cleaning tools & solvents or new wafers;
wafer feed mechanism;
wafer alignment system;
thermocouple temperature control; and
fume control system.

As taught by U.S. Pat. No. 4,610,670, thermoplastic tubes containing fluid can be welded by flattening the tubes. Although the same amount of pvc is cut when welding either round or flattened tubing, the wafer takes less time to cut flattened tubing so the rate of heat loss from the wafer is higher. This effect results in a very significant temperature drop as the tubes are welded.

If sterility is to be assured in the resulting weld this temperature drop must be minimized. The makeup energy required must come from one or both of two sources:

1. the transfer of energy stored in the wafer, wafer holder, etc. or
2. electrical energy from the built-in resistance heater in the wafer.

Experiments have shown that the wafer gets most of the make-up energy during the weld from heat stored in the wafer and wafer holder and not from the conversion of electrical energy to heat via the resistance heater.

The only existing welding wafer is the one used on the DuPont "SCD". It consists of an etched type 302 stainless steel serpentine resistance element folded into a copper sheath. The circuit is insulated for the copper and the unit is held together by a high temperature adhesive (DuPont Pyrolux).

This existing technology is inadequate in a number of areas:

1. Wafers must be replaced prior to making each weld.
2. Wafer construction techniques and material limit welding temperatures to approximately 575 degrees F., making it impossible to weld polyurethane tubing for example.
3. The wafer has very little thermal mass so that welding tubes or even breathing on the wafer during a weld could cause a severe temperature drop, possibly resulting in a non-sterile weld.
4. The wafer does not address the special problems associated with welding flattened tubing.
5. The wafer is mechanically weak and therefore is very difficult to clean and re-use.

SUMMARY OF INVENTION

An object of this invention is to provide a wafer and method of using the wafer which overcomes the above disadvantages.

A further object of this invention is to provide such a wafer which utilizes a non-stick surface and has high heat storage capacity and very high thermal limit in a rugged unit.

A still further object of this invention is to provide such a wafer which compensates for the weakness induced in welded tubes by the process of welding the tubes in a flattened state.

In accordance with this invention the wafer is in the form of a thin plate-like insulated core having a resistance circuit whereby the wafer may be heated to a temperature sufficiently high to melt through the tubes for thereby cutting the tubes.

The core may be of a ceramic material or may be metallic with a ceramic layer. In the preferred form of this invention a glass coating is provided over the resistance circuit and a cladding, such as copper clad is provided over the glass coating. The outer surface of the wafer, particularly in the areas which contact the tube may also be coated with glass to provide a non-stick surface.

In the preferred practice of this invention the wafer is used in a linear type weld cycle which utilizes the stubs from the unused portions of the tubes for contacting the wafers and having the residue on the wafers adhere to the stubs so that the residue may thereby be readily removed from the wafer. Such an arrangement, particularly in connection with the non-stick outer surface permits the wafer for all intents and purposes to be a permanent wafer by permitting an extremely long life for the wafer rather than requiring replacement as is necessary with the prior art.

THE DRAWINGS

FIG. 2 is a perspective view schematically showing one step of operation in conjunction with the residue removal from the wafer in a modified weld cycle;

FIGS. 3–4 show further steps of operation in the cycle of FIG. 2;

FIG. 5 is a perspective view of a wafer in accordance with this invention;

FIGS. 6–7 are side elevation and top plan views of the wafer shown in FIG. 5;

FIG. 8 is a cross-sectional view taken through FIG. 7 along the line 8—8;

FIG. 9 is a perspective view of a yet another form of wafer in accordance with this invention;

FIGS. 10–11 are side elevation and top plan views of the wafer shown in FIG. 9;

FIG. 12 is a cross-sectional view taken through FIG. 11 along the line 12—12;

FIG. 13 is a perspective view of a modified form of wafer in accordance with this invention;

FIGS. 14–15 are side elevation and top plan views of the wafer shown in FIG. 13; and FIGS. 16–17 are cross-sectional views of modified cutting areas for wafers in accordance with this invention.

DETAILED DESCRIPTION

Figure 1A:
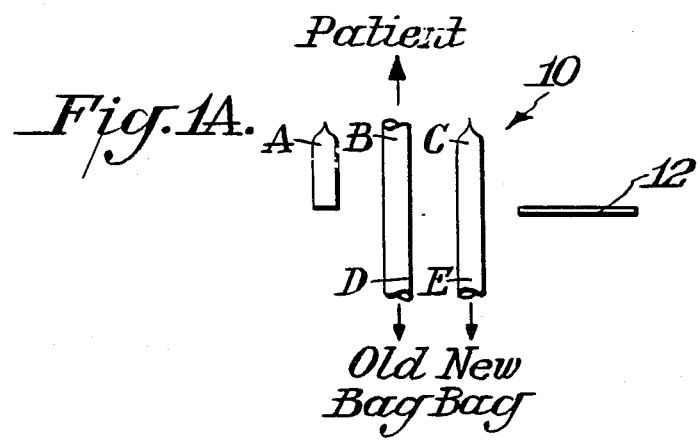
FIGS. 1A–1E are schematic views showing the steps involved in a linear type weld cycle in accordance with this invention.
Figure 1B:
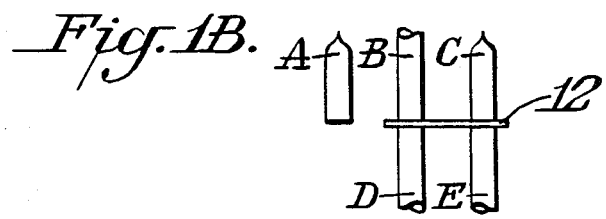
Figure 1C:
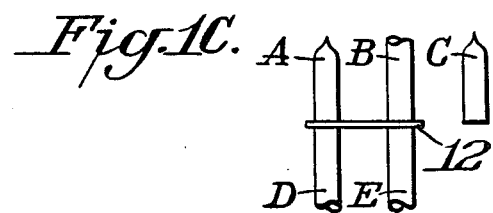
Figure 1D:
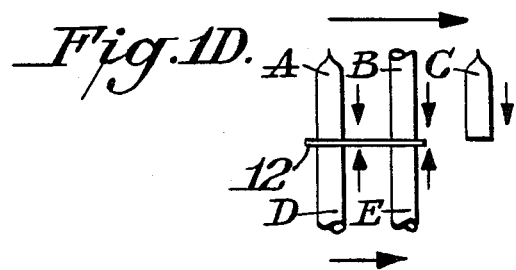
Figure 1E:
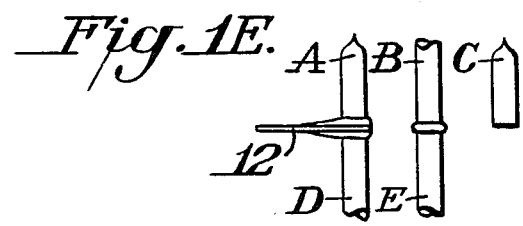

The wafer which is the subject of this invention may be used in any type tube splicer such as in the aforenoted patents or in the SCD system. It is preferred however, that the wafer be used in a linear type weld cycle such as illustrated in FIG. 1 where both tubes follow the same path onto and leaving the wafer. This allows the severed tube ends of the pre-weld tubing to be specially contoured so as to minimize the possibility of forming a hole at the folded corners of the tubes. FIGS. 2–4 exemplify a further preferred welding cycle for the practice of this invention.

FIG. 1 illustrates schematically the steps utilized in the linear type weld cycle of this invention. As shown therein, the arrangement 10 includes a stub A which remains from the previous weld operation. The arrangement also includes a second holder into which is inserted a tube having portion B leading to the patient and an opposite portion D leading to the old bag. Further the arrangement includes a tube having a portion C and a further portion E leading to the new bag. As shown in FIG. 1, arrangement 10 also includes wafer 12. Initially, as shown in FIG. 1A, the various tubes are placed in a pair of side-by-side holders with portions A, B and C being in one holder and portions D and E in another holder. In the preferred practice of this invention, wafer 12 is stationary and the two holders are movable. As shown in FIG. 1B the holders and their tubes are then moved so that wafer 12 cuts through tube B-D and tube C-E to separate the tubes into four individual sections. The cutting operation is accomplished by heating wafer 12 so that the heated wafer readily cuts through the plastic tubes. When all of the tubes are cut the holder having tubes A, B and C accelerates while the holder having tubes D and E either pauses or continues moving at a slower speed. This causes a realignment so that tube section D now becomes aligned with stub A and tube sections B and E become aligned with each other while tube section C is not aligned with any other tube and is no longer in any contact with wafer 12. See FIG. 1C. FIG. 1D next shows the relative position of the components when the two holders are moved toward each other. As a result of such movement tube sections B and E are butt welded together and tube sections A and D are pressed into contact with wafer 12. It is noted that in the step of FIG. 1E wafer 12 is disposed only between tube sections A and D. Wafer 12 is heated so that a large melt pool of the plastic tubing is formed by virtue of tube sections A and D being in contact with wafer 12. As shown in this step the holders are no longer in motion and wafer 12 is permitted to cool down. The welded tube B-E is then removed. Stub A is next removed which would peel off any residue which had been on wafer 12 and similarily stub D is removed to peel off residue on its side of wafer 12. Stub C would then remain to be used in the next welding operation.

FIGS. 2–4 show a variation of the linear weld system shown in FIGS. 1A–1E. As illustrated in FIGS. 2–4, the removal of the residue is achieved without utilizing a stub from a previous operation. Initially sections C-E form a single tube in round grooves 11, 13 of side-by-side holders 14, 16. Similarly, sections B-D are in the form of a single tube across round grooves 18, 20 in holders 14, 16. The holders 14, 16 are moved to effect a cut of the tubes by wafer 12 in the manner previously described. The cut sections are then realigned and tube sections B-E are butt welded. FIG. 2 illustrates the position of the various components after the cut has been made when tube sections B-E are butt welded together. As shown therein tube section D remains off set from the butt welded sections as does tube section C. FIG. 3 illustrates the stage of operation wherein the butt welded tube B-E has been removed from the holders 14, 16. Stub D is placed in the V-shaped groove 17, in contact with wafer 12 and stub C is similarly placed in the corresponding V groove 21 of its holder 14 in contact with wafer 12 is again heated to create a melt pool so that any residue on the wafer adheres to the melt pool. The wafer is cooled to less than 150° F. The residue may then be removed by simply removing the stubs as illustrated in FIG. 4. If desired, the residue may simply be peeled directly from the wafer with for example the users fingernail.

An advantage of the present invention is that the residue is not only removed from the wafer but also functions to seal off the stub ends which prevents the leakage of any toxic material that may be in the stub ends.

The following examples illustrate the practice of this invention using the pass through type operation of FIG. 1 and the reversing type welder operation of FIGS. 2–4.

EXAMPLE 1

In one embodiment, a welder is designed to weld flattened or round plastic tubing using a linear type cycle. The weld cycle is shown in FIG. 1.

A second tube is deliberately placed in the clamps prior to welding. After the weld is complete, this extra tube and one of the "stub-ends" normally formed during welding will remain in contact with the wafer at end-of-weld. The wafer is cleaned by allowing the wafer and weld to cool in this position. When cool, the polymeric residue on the wafer will come off with the stubs as they are removed. The cycle shown in FIG. 1 is a "pass-thru" cycle. The tubes start on one side of the wafer, the tubes are passed through the wafer and the welded tube appears on the far side of the wafer, but the above wafer cleaning technique is usable on either a pass-thru or a reversing type welder (as in FIGS. 2–4).

EXAMPLE 2

In another embodiment a welder is constructed using the cycle of FIGS. 2–4. After the weld has taken place and the tube clamps open. The welded tubing is removed and then the wafer heating actuating button is pressed. This causes the wafer to heat up again to about 400° F. The temperature re-melts the residue on the sides of the wafer. While the wafer is at this temperature, the stub ends from the weld just made are removed from their normal positions and pressed against the sides of the wafer (FIG. 3). The wafer and tubes are then allowed to cool in this position until the wafer reaches 150° F. or cooler. At this point the stubs are peeled away from the wafer removing the residue (FIG. 4). The large mass of plastic at the ends of the stubs effectively seals them. If done correctly, this technique even seals round tubes.

FIGS. 5–8 show one embodiment of wafer 12 in accordance with this invention. As indicated therein wafer 12 includes a core 22 made of a metallic material such as steel. An insulating layer of a suitable material such as ceramic is deposited on the core 22 and fired to prevent shorting out the heater element. As illustrated in FIGS. 5 and 8, however, a glass layer 24 is formed directly on core 22. For example, 0.5 mil glass may be formed on 1 mil stainless steel core. Alternatively, the core and insulating layer may be combined by using a thin ceramic substrate as the core. In either version, a high temperature insulated plate-like core is formed.

Using thick film technology a resistance circuit 26 is laid down on the ceramic substrate and fired. The circuit 26 can also be configured as a serpentine path of a film paste which would provide the ability to selectively tailor the watt density across the wafer. This provides a way to compensate for heat sinks such as wafer holders or contacts.

As shown in FIG. 8, a thin glass overcoat 28 seals the circuit so that the later described copper cladding 30 does not short out the circuit. The glass need only be for example 0.001 inches thick. The wafer is then fired again.

Using any conventional technique a thermal conductive metal cladding 30 of a suitable heat sink material, such as copper, silver, gold, steel or nickel, is selectively applied to the wafer. The cladding is deposited such that it forms a massive heat sink around the weld area. This generally minimizes the temperature drop caused by melting of the tubes by welding.

As shown in FIGS. 5-8 the open area 32 of the cladding material 30 is the area which contacts and cuts through the tubes. As also shown in FIGS. 5-8 a pair of holes 36 are provided in the copper cladding for permitting electrical contact to be made with the resistance circuit 26.

A significant advantage of this invention is that the wafer and more particularly the portion of the wafer which makes cutting contact with the tubes is extremely thin. This dimension is best shown in FIG. 8 as indicated by the letter "F". For example, the thickness F would, in the preferred form of the invention, be less than 5 mils thick and as thin as only 1 mil. This allows precise welding of thin wall small diameter tubes.

If desired, the finished wafer may then be coated with a thin layer of glass (FIGS. 9-12) and then fired. The glass is then polished to provide a release surface. Typical tubing materials would generally be unable to adhere to such a surface.

In the variation of this invention of FIGS. 9-12 the wafer 12 has a glass coating 34 on all of its exposed surfaces except for holes 36 so that the electrical contact 38 (FIG. 12) can be made through hole 36. The advantage of this embodiment is to provide a smooth polished exterior surface over substantially the entire exposed portions of wafer 12. If desired the glass coating might simply be in the channel portion 32 of wafer 12 which is where the contact is made with the tubes being cut. Alternatively, the glass outer surface may be over the clad area 22 up to a portion immediately short of holes 36, instead of the entire exposed surface as in FIGS. 9-12.

FIG. 9 shows a further variation wherein the contact area 32 is tapered to facilitate the cutting of the tubes.

The modification of FIGS. 9-12 includes only a single resistance circuit 26 with one set of holes 36 in its upper surface for electrical contact 38 rather than the two resistance circuits 26 and two sets of holes 36 of FIGS. 5-8.

The embodiment of FIGS. 9-12 also differ from FIGS. 5-8 in that a ceramic layer 25 is formed on core 22 with resistance circuit 26 deposited thereon. Then a further ceramic layer 27 is provided, all of which are covered by glass overcoat 34.

The wafers 12 of FIGS. 5-12 result in a tube which is cut in a uniform manner as indicated by tube end 40 of FIG. 9. It has been found however, that when such tubes are clamped during the prior art butt welding operation tube distortion results. As a result, there is difficulty in forming a sterile connection during the butt welding. In order to avoid this difficulty, applicants have discovered that it is possible to contour the wafer so as to form a non-uniform cut which compensates for such distortion.

FIGS. 13-15 show one embodiment of this invention wherein the wafer 12 results in a tube end 42 having the contoured cut end as illustrated in FIG. 13. The embodiment of FIGS. 13-15 is generally similar to that of FIGS. 5-8. A difference however, is that a portion of the wafer contains copper cladding extension 44 which results in a pair of channels 46, 46 being formed in the exposed surface of wafer 12. These channels cause the cut-out recess 48 to result in the upper edge or cut end 42 of the tube. Extension 44 is also tapered to facilitate the cutting.

FIGS. 16-17 show variations of wafers 12 wherein the glass overcoat has portions 50 (FIG. 16) or 52 (FIG. 17) in the cutting area to result in yet other forms of contoured cuts for tubes 54, 56.

Although not illustrated a further feature of this invention which is used either in combination with the tube contour forming means of the wafer (e.g. extensions 46, 50 or 52) or separately, is to form the clamps on the tube holders of contoured rather than straight shape. As a result the clamps would also function to impart a contour to the cut ends of the tubes.

A number of distinct advantages result from the present invention. For example, because of the glass exterior the outer surface of the wafer may be smooth and polished so that the wafer is self-cleaning and need not be replaced between welds. A further advantage is that the welding unit uses the stub ends of the non-welded tubes as an aid in removing the residue from the sides of the wafer which also increases the wafer life so that the wafer is thus a permanent wafer rather than a disposable as with the prior art.

The invention also contemplates in one embodiment utilizing an extra tube to provide a convenient stub end for removing residue from one side of the wafer. The weld cycle in which the stub ends from the weld are used is such as to clean the sides of the wafer while at the same time sealing the stub ends.

In general, the wafer structure includes a ceramic or metallic core onto which is placed a resistance circuit for heating the wafer to the proper temperature as voltage is applied. Copper or other suitable material is plated or mechanically attached adjacent the weld area to minimize temperature drop in the wafer as the weld is taking place and to mechanically stiffen the wafer. An additional outer layer of glass or other non-oxidizing surface is preferably deposited in the weld area to provide a non-stick surface as noted above. The glass may be polished to a high degree of smoothness, but not necessarily of optical flatness.

The wafer because of its selective cladding causes the pre-weld stub ends to have a special non-flat shape which compensates for the normal weaknesses associated with flat tube welding. Because of the wafer's structure, the wafer is capable of welding tubing at temperatures uniformly close to the bacteria kill temperature without the usual unacceptable temperature drop. Moreover, the wafer of this invention makes stronger welds in PVC because of its ability to operate at low weld temperatures without the risk of large temperature drops associated with current wafers. This thus limits the degree of polymer degradation due to the heat and makes fume control unnecessary.

A particularly notable feature of this invention is the ability to heat the wafer to temperatures far in excess of those utilized in the prior art. In this respect, the prior art was limited to tubing made for example of low melt temperature polymers, such as pvc. The above noted prior art for example, indicates that the temperatures utilized are from 500°–750° F. The present invention however, permits the wafer to be used with materials other than pvc such as polyurethane in which the cutting is set at 850° F. Thus, the invention may be considered as permitting wafer temperatures above 750° F. and even in excess of 1,000° F.

What is claimed is:

1. A wafer for cutting plastic tubes which are to be butt welded together, said wafer being of multilayer plate-like shape comprising a high temperature insulating core, a resistance circuit on said core for heating the wafer to a temperature sufficiently high to melt through the tubes for thereby cutting the tubes, means for applying voltage to said resistance circuit for effecting said heating, said wafer including a tube contacting zone, contour forming means in said contacting zone for forming a contoured cut in the tubes, a thin glass overcoat provided over said resistance circuit, and a metal cladding provided over said glass overcoat, said cladding also being in a portion of said contacting zone to comprise said contour forming means.

2. A wafer for cutting plastic tubes which are to be butt welded together, said wafer being of plate-like shape, said wafer having a tube contacting zone with means for cutting through the plastic tubes, a thin smooth overcoat on the exposed surface of said tube contacting zone, said overcoat being made of glass, and said tube cutting zone including said overcoat having a thickness of less than 5 mils, said wafer being of multilayer construction including a high temperature insulating core, a resistance circuit on said core for heating the wafer to a temperature sufficiently high to melt through the tubes for thereby cutting the tubes, and means for applying voltage to said resistance circuit for effecting said heating.

3. The wafer of claim 2 wherein said resistance circuit is on one side said core, a second resistance circuit being provided on the other side of said core, said overcoat being provided over each resistance circuit, a thermal conductive metal cladding being provided over each said overcoat, and said resistance circuits being exposed through terminal openings in said cladding.

* * * * *